United States Patent [19]
Fodor et al.

[11] Patent Number: 5,324,633
[45] Date of Patent: Jun. 28, 1994

[54] METHOD AND APPARATUS FOR MEASURING BINDING AFFINITY

[75] Inventors: Stephen P. A. Fodor, Palo Alto; Laura T. Mazzola, Redwood City, both of Calif.

[73] Assignee: Affymax Technologies N.V., Curacao, Netherlands

[21] Appl. No.: 796,947

[22] Filed: Nov. 22, 1991

[51] Int. Cl.⁵ .................. G01N 33/543; G01N 33/566
[52] U.S. Cl. .......................................... 435/6; 435/4; 435/7.1; 435/970; 435/973; 435/975; 436/164; 436/518; 436/527; 436/531; 436/808; 436/809; 436/810; 436/823; 422/52; 422/82.06; 422/99; 530/333; 530/334
[58] Field of Search ................ 436/517, 518, 527, 531, 436/89, 164, 171-172, 808-810, 823; 435/6, 7.1, 7.92, 968, 970, 973, 975, 4; 422/52, 82.06, 99, 131, 134; 530/333, 334; 935/88

[56] References Cited

U.S. PATENT DOCUMENTS 4,072,576  2/1978  Arwin et al.
5,143,854  9/1992  Pirrung et al. .................. 436/518

FOREIGN PATENT DOCUMENTS 0127438  5/1984  European Pat. Off. ...... G01N 33/54
WO83/00991  11/1986  PCT Int'l Appl. .......... G01N 33/53
9210092  6/1992  World Int. Prop. O. .......... 436/518

OTHER PUBLICATIONS

Ajayaghosh et al. *Indian Journal of Chemistry*, vol. 27B, Nov. 1988, pp. 1004–1008.
Frank et al, *Tetrahedron*, vol. 44, No. 19, Nov. 1988, pp. 6031–6040.
Geysen et al. *Journal of Immunological Methods*, vol. 102 (1987) pp. 259–274.
Haridasan et al, *Proc. Indian Natn. Sci. Adad.*, vol. 53A, No. 6 (1987) pp. 717–728.
Hood et al, *Immunology*, 2d edition (1984) The Benjamin/Cummings Publishing Company, Inc. pp. 58–73.
Chuang et al., *J. Lab. Clin. Med.* (Sep. 1978) pp. 483–496.
Scatchard, *Equilibrium in Solutions/Surface and Colloid Chemistry*, Harvard University Press, 1976, pp. 242–248.
Portmann et al., *Immunochemistry* (1975) 12:461–466.
Smith et al., *Immunochemistry* (1977) 14:565–568.
Geysen et al., *Proc. Natl. Acad. Sci. USA* (1984) 81:3998–4002.
Lowe, *Trends in Biotech.* (1984) 2:59–65.
Lowe, *Biosensors* (1985) 1:3–16.
Getzoff et al., *Science* (1987) 235:1191–1196.
Geysen et al., *Peptides: Chemistry and Biology*, Marshall, ed., Proc. 10th Am. Peptide Symp., May 23–28, 1987, pp. 519–523.
Geysen et al., *Science* (1987) 235:1184–1190.
Geysen et al., *Molecular Recognition* (1988) 1:1–10.
Lowe et al., *Methods in Enzymology, vol. 137: Immobilized Enzymes and Cells*, Academic Press, Inc., 1988, pp. 338–348.
Goldstein et al., *Biophys. J.* (1989) 56:955–955.
DeLisi, *Mol. Immunol.* (1981) 18:507–511.
Erickson et al., *Biophys. J.* (1987) 52:657–662.
Erickson et al., *Biochemistry* (1991) 30:2357–2363.
DeLisi et al., *Proc. Natl. Acad. Sci. USA* (1981) 78:5569–5572.
Sutherland et al., *J. Immun. Meth.* (1984) 74:253–265.

*Primary Examiner*—Esther L. Kepplinger
*Assistant Examiner*—Carol A. Spiegel
*Attorney, Agent, or Firm*—Vern Norviel; Kevin Kaster; Joe Liebeschuetz

[57] ABSTRACT

A method and device for measuring the binding affinity of a receptor to a ligand. According to one aspect of the invention, arrays of polymers are synthesized or immobilized on a substrate (212). The array of polymers is exposed to a fluorescently-labelled receptor in solutions of varying concentration. The fluorescence intensity of the labelled receptor is measured by way of, e.g., a photon counter using a confocal microscope (316). Binding affinity is determined through analysis of the relationship between fluorescence intensity and the solution concentration of the receptor. On-rates are measured as a kinetic increase in surface fluorescence intensity, and the on-rate constant rate extracted from fits to the data.

21 Claims, 8 Drawing Sheets

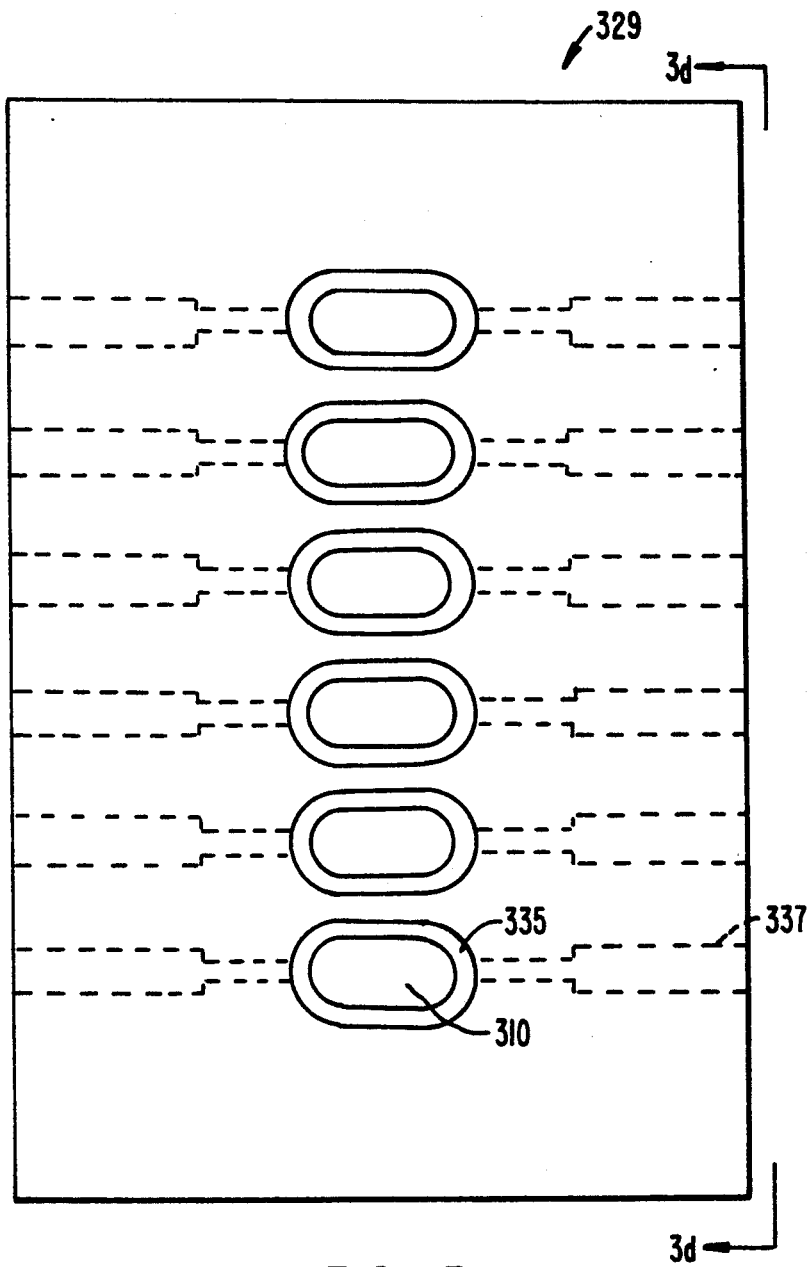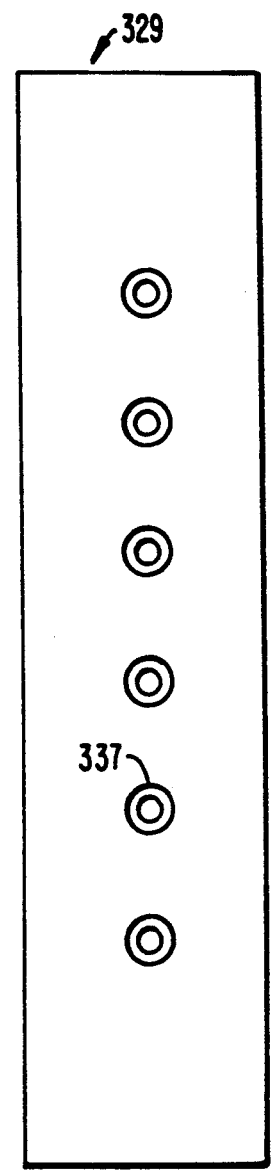
FIG. 3c.
FIG. 3d.

METHOD AND APPARATUS FOR MEASURING BINDING AFFINITY

BACKGROUND OF THE INVENTION

The present invention relates to the field of ligand-/receptor interaction evaluation. More specifically, in one embodiment the invention provides a novel system for the determination of the binding affinity of a receptor to a surface-bound, high-density ligand array and vice versa (ligand to bound receptor). Due to the nature of the immobilized array, this system also permits measurements of both on- and off-rates of receptor binding. In a particular embodiment, the present invention provides a method and device for quantitation of binding affinity utilizing fluorescence intensity data from labelled receptors bound to peptides which have been synthesized or immobilized on a solid support. In another embodiment, the present invention provides a method for determining the fidelity of synthesis of peptides by comparing the fluorescence intensity of a receptor bound to an array to the fluorescence intensity of the receptor bound to an array of known purity and composition.

Techniques have recently been introduced for synthesizing large arrays of different peptides and other polymers on solid surfaces. For example, in Pirrung et al., PCT Publication No. WO 90/15070, incorporated herein by reference for all purposes, a technique is disclosed for generating arrays of peptides and other materials using, for example, light-directed, spatially-addressable synthesis techniques. See also U.S. patent application Ser. No. 07/624,120 (Fodor et al.) which discloses, among other things, a method of gathering fluorescence intensity data, various photoprotective groups, masking techniques, and automated techniques for performing light-directed, spatially-addressable synthesis techniques. Because of their relationship to semiconductor fabrication techniques, these methods have come to be referred to as "Very Large Scale Immobilized Polymer Synthesis," "VLSIPS TM" synthesis technique. Such techniques have met with substantial success in, for example, screening various ligands such as peptides to determine their relative binding affinity to a receptor such as an antibody.

While meeting with substantial success, such techniques generally provide a qualitative estimate of binding affinity for a ligand-receptor pair as well as the relative order of affinities for a multi-ligand substrate. Other techniques of measuring binding affinity provide only indirect indications of binding affinity.

It is desirable to provide a direct method and device for more precisely determining the binding affinity of a receptor to a specific ligand substrate synthesized in a multi-ligand array.

SUMMARY OF THE INVENTION

A novel method and device for quantitatively evaluating the binding affinity of a receptor/ligand substrate is provided by virtue of the present invention. The method and device are particularly suited for application to solid-phase synthesis techniques such as the VLSIPS TM technique, as well as bead or pin-based techniques.

According to one preferred embodiment of the invention, an array of ligands, particularly polymers such as peptides, is formed on a substrate at predetermined locations. The ligands are exposed to a receptor such as an antibody or series of antibodies, one or more of which are labelled with a fluorescent label, such as fluorescein. Fluorescence intensity data at or near steady-state or equilibrium are gathered from the substrate at a variety of locations within the predetermined substrate pattern, providing a measure of receptor binding to the surface-bound ligands. The process is repeated with a series of different receptor concentrations. Based on the fluorescence intensity data for the solutions of varying concentrations, it becomes possible to extract quantitative information regarding the binding affinity of the receptor to various ligand substrates. The data obtained from substrate-bound ligand data herein closely approximate solution behavior of the ligand/receptor pair.

In one embodiment, the invention provides a method of determining the binding affinity of a receptor/ligand pair. The method includes the steps of exposing a labelled receptor to one or more ligands on the surface of a substrate to a labelled receptor at a first solution concentration of receptor; exposing the ligands on the surface of a substrate to the labelled receptor at a second receptor concentration; measuring indicia related to the number of receptor molecules bound to the ligands; and based on the indicia related to the number of receptor molecules bound to the ligands, determining a binding affinity of the ligands to the receptor.

A further understanding of the nature and advantages of the inventions herein may be realized by reference to the remaining portions of the specification and the attached drawings.

BRIEF DESCRIPTION OF THE DRAWINGS

FIGS. 3a, 3b, 3c, and 3d illustrate a device and method for gathering fluorescence intensity data as a function of location on a substrate;

DESCRIPTION OF THE PREFERRED EMBODIMENTS

Contents

Figure 1:
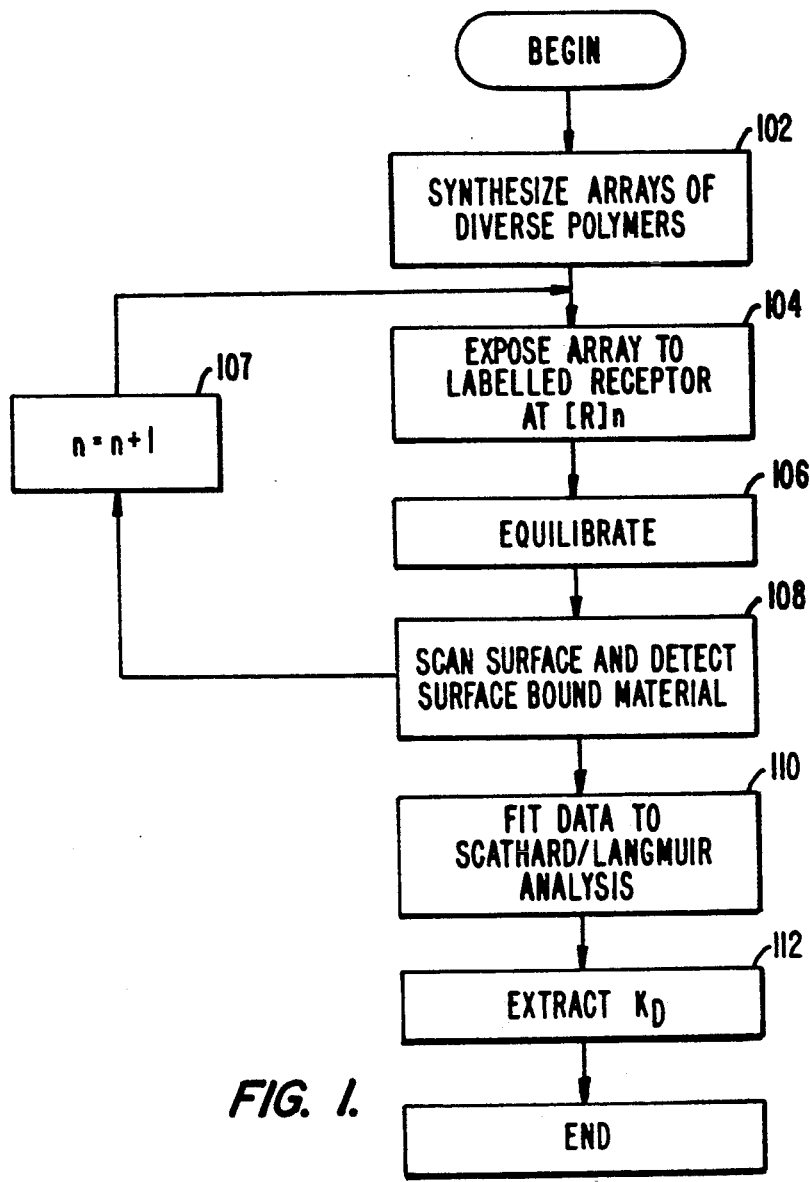
FIG. 1 is an overall flow diagram illustrating a process for determining the relative binding affinity of a ligand and a receptor.

I. Glossary
II. Detailed Description
III. Examples
IV. Conclusion

I. Glossary,

The following terms are intended to have the following general meanings as they are used herein:

1. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., steroids etc.), hormone receptors, peptides, enzymes, enzyme substrates, cofactors, drugs, lectins, sugars, oligonucleotides, nucleic acids, oligosaccharides, proteins, and monoclonal antibodies.

2. Monomer: A member of the set of small molecules which are or can be joined together to form a polymer. The set of monomers includes but is not restricted to, for example, the set of common L-amino acids, the set of D-amino acids, the set of synthetic and/or natural amino acids, the set of nucleotides and the set of pentoses and hexoses. The particular ordering of monomers within a polymer is referred to herein as the "sequence" in the polymer. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the analysis of molecules containing sequences of monomers such as amino acids, but could readily be applied in the analysis of other polymers. Such polymers include, for example, both linear and cyclic polymers of nucleic acids, polysaccharides, phospholipids, and peptides having either $\alpha$-, $\beta$-, or $\omega$-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in copending application Ser. No. 796,727, filed on the same date as the present application, entitled "POLYMER REVERSAL ON SOLID SURFACES," incorporated herein by reference for all purposes.

3. Peptide: A polymer in which the monomers are alpha amino acids and which are joined together through amide bonds and alternatively referred to as a polypeptide. In the context of this specification it should be appreciated that the amino acids may be the L-optical isomer or the D-optical isomer. Peptides are two or often more amino acid monomers long, and often more than 20 amino acid monomers long. Standard abbreviations for amino acids are used (e.g., P for proline). These abbreviations are included in Stryer, *Biochemistry*, Third Ed., 1988, which is incorporated herein by reference for all purposes. Small case and large case letters are utilized to differentiate the D-isomer and L-isomer, respectively.

4. Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a mediating linker. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "ligand receptor pair" is formed when two macromolecules have combined through noncovalent molecular recognition to form a complex.

Specific examples of receptors which can be investigated by this invention include but are not restricted to:

a) Microorganism receptors: Determination of ligands which bind to receptors, such as specific transport proteins or enzymes essential to survival of microorganisms, is useful, as in the discovery of a new class of antibiotics. Of particular value would be antibiotics against opportunistic fungi, protozoa, and those bacteria resistant to the antibiotics in current use.

b) Enzymes: For instance, determination of the binding site of enzymes such as the enzymes responsible for cleaving neurotransmitters is useful. Also of value would be determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines in which the immunogen is based on one or more of such sequences or may lead to the development of related diagnostic agents or compounds useful in therapeutic treatments such as for autoimmune diseases (e.g., by blocking the binding of the "self" antibodies). For purposes of the present invention, "antibody" includes a whole antibody or an antibody fragment (Fab or (Fab)$_2$).

d) Nucleic Acids: Sequences of nucleic acids may be synthesized to establish DNA or RNA binding sequences.

Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

5. Substrate: A material having a rigid or semi-rigid surface. In many embodiments, at least one surface of the substrate will be substantially flat, although in some embodiments it may be desirable to separate synthesis regions physically for different polymers with, for example, wells, raised regions, etched trenches, or the like. According to other embodiments, small beads, such as beads with peptides on the surface (which, in some embodiments, may be released upon completion of the synthesis), are employed. In other embodiments, however, the substrate need only be semi-soluble, i.e., a substrate, such a polyethylene glycol (PEG) that is a solid in some but not all solvents.

6. Protective Group: A material which is bound to a monomer unit and which may be selectively removed therefrom.

7. Predefined Region: A predefined region is a localized area on a substrate which is, was, or is intended to be used for formation of a selected polymer and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct polymer sequence is synthesized is smaller than about 1 cm² or less than 1 mm². In preferred embodiments the regions have an area less than about 10,000 $\mu m^2$ or, more preferably, less than 100 $\mu m^2$ and may, in some embodiments be less than 10 $\mu m^2$. Within these regions, the polymer synthesized therein is preferably synthesized in a substantially pure form.

8. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is 5% pure, more preferably more than 10% pure, preferably more than 20% pure more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

II. Detailed Description

FIG. 1 is an overall flow chart illustrating a process for determining the binding affinity of a receptor to a ligand and, in particular, a process for determining the binding affinities of a receptor to an array of ligands synthesized on a substrate. All operations herein are preferably performed at constant and substantially atmospheric pressure and ambient temperature, although in some embodiments it will be of interest to determine binding affinity under a variety of conditions and the experiment will be repeated at, for example, different temperatures.

As shown at step 102, an array or arrays of ligands such as peptides are synthesized on a support, or fully synthesized polymers are immobilized on a support. The method may be sequentially performed on one array or may be done simultaneously on a series of duplicate arrays. In some embodiments, duplicate arrays are synthesized on separate substrates.

The method of forming the arrays will vary from one application to another. According to preferred embodiments, the ligands are formed according to the light-directed synthesis techniques of Pirrung et al., WO 90/15070, previously incorporated by reference for all purposes. Other methods will be used according to some embodiments such as the "pin" method described in Geysen, or the method described in copending application Ser. No. 796,243, filed on the same day as the present application, and incorporated herein by reference for all purposes. Whether the ligand is synthesized on or presynthesized and then immobilized on the surface is not essential to the present invention, however.

At step 104 the array or arrays of polymers are exposed to a receptor at a first solution concentration $[R]_1$. According to some embodiments the receptor is marked with an appropriate label such as a fluorescein tag. Fluorescent tags are preferred because the measurements herein are usually taken with a receptor solution in contact with the immobilized ligands to ensure that the immobilized ligand are in equilibrium with the receptor. By "equilibrium" herein it is intended to mean that the amount of receptor bound to the ligand does not change appreciably over time. Confocal microscopy provides one preferred method of distinguishing between surface receptor fluorescence and background fluorescence from bulk solution receptors, due to the limited depth of field of a confocal microscope. Because the microscope cannot completely exclude fluorescence from bulk solution, contributions of the bulk fluorescence can be eliminated by comparing areas of derivatized and underivatized substrates. This method for eliminating background fluorescence may not be accurate at high receptor concentrations, when non-specific receptor binding to underivatized substrates becomes non-negligible.

In various embodiments, the substrate and first receptor (either labelled or unlabelled) are exposed to a second labelled receptor which binds to the first receptor, preferably at multiple locations. In this embodiment, it is not necessary to label the first receptor. This procedure can be used to provide signal amplification and, therefore, an improved signal-to-noise ratio from the data.

At step 106 the array of the polymers is exposed to the receptor, for a time sufficient to allow receptor-ligand interaction, preferably to equilibrium conditions, and at step 108 the fluorescence intensity of the receptor at each of the concentrations $[R]_n$ is determined for each of the ligands on each array. The process can be repeated for each receptor concentration by repeating steps 104 to 108, as indicated by step 107.

It will be recognized that while the invention is illustrated herein by way of a serial process in which the receptor concentration is varied while contacting a single array of polymers, other embodiments will find wide application. For example, in preferred embodiments, a plurality of duplicate (or near duplicate) arrays can be synthesized in different regions on a substrate, and by simultaneously contacting all of the arrays with receptor solutions of different concentrations it becomes possible to reduce substantially the time required for performing the process. In embodiments where a single array of polymers is utilized, it is preferred that the receptor concentration be increased during the process, rather than decreased, because bound receptor may be difficult to remove.

At step 110 this information is fit to analysis equations or otherwise processed for determination of the binding affinity of the receptor to the various ligands on the substrate and at step 112 the $K_d$ values, among others, are extracted. In a most preferred embodiment the data are used to determine binding affinity by determining the slope of a best fit line through a plot having, on the y-axis, the ratio of fluorescence intensity to receptor concentration and, on the x-axis, the fluorescence intensity. It will of course be recognized that in most embodiments, a line will not actually be mechanically "plotted" and, instead, such operations will be conducted in an appropriately programmed digital computer, using discrete logic, or the like. To facilitate comparison to other experiments, one can plot normalized fluorescence intensity on the y axis or receptor concentration on the x axis. A "normalized" plot has all intensity scaled to saturation intensity.

The exact sequence of steps described above can be varied without departing from the scope of the invention herein. For example, after exposing the polymer array to the receptor at a first concentration, it may be desirable to extract the fluorescence intensity information for the array at this initial concentration before proceeding with different concentrations. Based on information from the array exposed to the receptor at the first concentration, it may become evident that the receptor in question does not bind in any appreciable way to certain ligands. Accordingly, in subsequent steps, a ligand array may be synthesized which eliminates the ligands without appreciable binding affinity. The subsequent arrays may have other attributes, such as increased synthesis area for the ligands of primary interest.

In some embodiments, one or several fully pre-synthesized ligands are immobilized on the surface of the substrate in selected regions. For instance, such peptides can serve as standards for fidelity of synthesis of other polymers. These pre-synthesized ligands can be duplicates of one or more of the peptides which have been synthesized on the substrate. By comparison of the binding affinity of these pre-synthesized ligands to the ligands which are synthesized on the substrate directly, it will be possible to determine if the synthesized peptides are of less than desired purity, and to estimate the degree of impurity of the substrate synthesized ligands.

Figure 2:
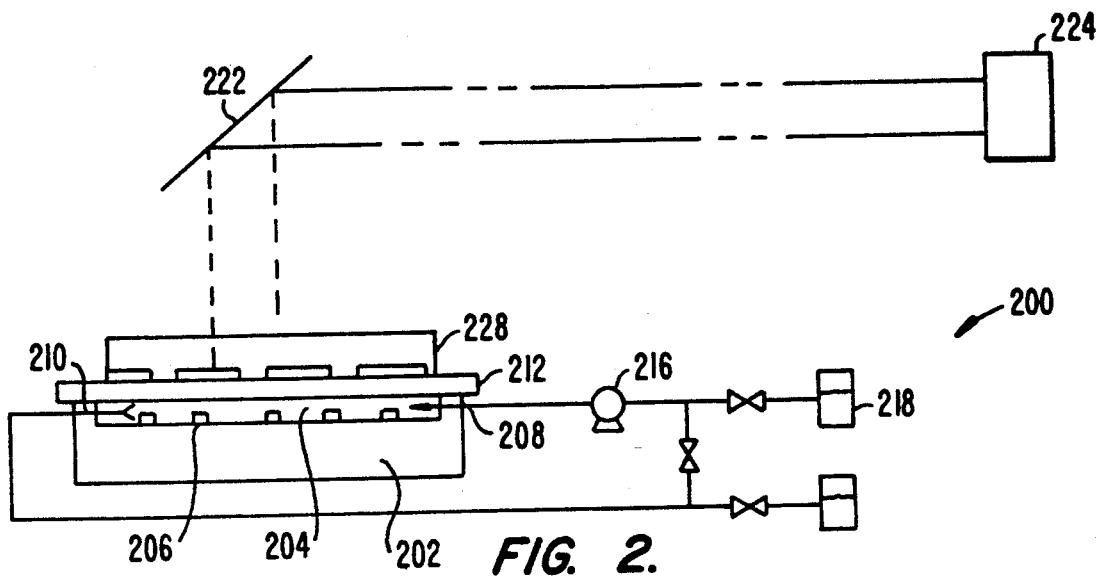
FIG. 2 illustrates a device and process for forming diverse polymer sequences on a substrate.

FIG. 2 schematically illustrates a preferred embodiment of a reactor system 200 for synthesizing polymers on the prepared substrate. It will be recognized that the system shown in FIG. 2 is only illustrative of the systems for synthesizing the polymers for use herein. For example, the polymers may be synthesized on a substrate in some embodiments using a channel block for directing the flow of reactants over a substrate in accordance with the techniques disclosed in copending application Ser. No. 796,243, entitled "VERY LARGE SCALE IMMOBILIZED POLYMER SYNTHESIS USING MECHANICALLY DIRECTED FLOW PATHS," previously incorporated herein by reference for all purposes.

The reactor system includes a body 202 with a cavity 204 on a surface thereof. In preferred embodiments the cavity 204 is between about 50 and 1000 $\mu$m deep with a depth of about 500 $\mu$m preferred. The bottom of the cavity is preferably provided with an array of ridges 206 which extend both into the plane of the Figure and parallel to the plane of the Figure. The ridges are preferably about 50 to 200 $\mu$m deep and spaced at about 2 to 3 mm. The purpose of the ridges is to generate turbulent flow for better mixing. The bottom surface of the cavity is preferably light-absorbing so as to prevent reflection of impinging light.

A substrate 212 is mounted above the cavity 204. The bottom surface of the substrate is attached to a photoremovable protective group, such as NVOC, nitroveratryloxy carbonyl with or without an intervening spacer molecule. The substrate is preferably transparent to a wide spectrum of light, but in some embodiments is transparent only at a wavelength at which the protective group may be removed (such as near UV in the case of NVOC). The substrate in some embodiments is a conventional microscope glass slide or cover slip. The substrate is preferably as thin as possible, while still providing adequate physical support. Preferably, the substrate is less than about 1 mm thick, more preferably less than 0.5 mm thick, more preferably less than 0.1 mm thick, and most preferably less than 0.05 mm thick. In alternative preferred embodiments, the substrate is quartz or silicon.

The substrate and the body serve to seal the cavity except for an inlet port 208 and an outlet port 210. The body and the substrate may be mated for sealing in some embodiments with one or more gaskets or O-rings. According to a preferred embodiment, the body is provided with two concentric gaskets and the intervening space is held at vacuum to ensure a leak-proof seal of the substrate to the gaskets. A mask 228 is placed on or near the substrate 212.

Fluid from storage 218 is pumped through the inlet port into the cavity by way of a pump 216 which may be, for example, a model no. B-120-S made by Eldex Laboratories. Selected fluids are circulated into the cavity by the pump, through the cavity, and out the outlet for recirculation or disposal. The reactor may be subjected to ultrasonic radiation and/or other method of stirring to aid in agitation in some embodiments.

For the sake of a compact system, a reflective mirror 222 may be provided for directing light from a light source 224 onto the substrate. Light source 224 may be, for example, a Xe(Hg) light source manufactured by Oriel and having model no. 66024. This form of lithography is referred to herein as proximity printing. As will be apparent from this disclosure, projection printing and the like may also be used according to some embodiments.

Light from the light source is permitted to reach only selected locations on the substrate as a result of the mask 228. Mask 228 may be, for example, a glass slide having etched chrome thereon. The mask 228 in one embodiment is provided with a grid of transparent locations and opaque locations and, in the case of a contact printing process, is preferably placed so that the side printed with the opaque regions is placed in direct contact with the substrate. Such masks may be manufactured by, for example, Photo Sciences, Inc. Light passes freely through the transparent regions of the mask, but is reflected from or absorbed by other regions. Therefore, only selected regions of the substrate are exposed to light.

In operation, the substrate is placed on the cavity and sealed thereto. All operations in the process of preparing the substrate are carried out in a room or enclosure lit primarily or entirely by light of a wavelength outside of the light range at which the protective group is removed. For example, in the case of NVOC, the room should be lit with a conventional dark room light which provides little or no UV light. All operations are preferably conducted at about room temperature.

A first wash solution for deprotection (without a monomer) is circulated through the cavity. The solution preferably, in the case of amino acid coupling, is of 5 mM sulfuric acid in dioxane solution which serves to keep exposed amino groups protonated and decreases their reactivity with photolysis by-products. Absorptive materials such as N,N-diethylamino 2,4-dinitrobenzene, for example, may be included in the deprotection fluid which serves to absorb light and prevent reflection and unwanted photolysis.

The slide is, thereafter, positioned in a light raypath from the mask such that first locations on the substrate are illuminated and, therefore, deprotected. In preferred embodiments the substrate is illuminated for between about 1 and 15 minutes with a preferred illumination time of about 10 minutes at 10–20 mW/cm$^2$ with 365 $\mu$m light. The slides are neutralized (i.e., brought to a pH of about 7) after photolysis with, for example, a solution of di-isopropylethylamine (DIEA) in methylene chloride for about 5 minutes.

The first monomer is then placed at the first locations on the substrate. After irradiation, the slide is removed, treated in bulk to add the first monomer, and then reinstalled in the flow cell. Alternatively, a fluid containing the first monomer, preferably also protected by a protective group, is circulated through the cavity by way of pump 216. If, for example, it is desired to attach the amino acid Y to the substrate at the first locations, the amino acid Y (bearing a protective group on its α-nitrogen), along with reagents used to render the monomer reactive, and/or a carrier, is circulated from a storage container 218, through the pump, through the cavity, and back to the inlet of the pump.

As the solution containing the monomer to be attached is circulated through the cavity, the amino acid or other monomer will react at its carboxy terminus with amino groups on the regions of the substrate which have been deprotected. Of course, while the invention is illustrated by way of circulation of the monomer through the cavity, the invention could be practiced by way of removing the slide from the reactor and submersing it in an appropriate monomer solution.

After addition of the first monomer, the solution containing the first amino acid is then purged from the system. After circulation of a sufficient amount of the DMF dimethylformamide methylene chloride such that removal of the amino acid can be assured (e.g., about 50× times the volume of the cavity and carrier lines), the mask or substrate is repositioned, or a new mask is utilized such that second regions on the substrate will be exposed to light and the light is engaged for a second exposure. This will deprotect second regions on the substrate and the process is repeated until the desired polymer sequences have been synthesized.

The process is repeated in preferred embodiments herein to synthesize substrates having duplicate peptide sequence arrays, or subarrays thereof. According to techniques described herein, some embodiments of the invention provide for synthesis of duplicate "copies" of the various polymer sequence arrays on a single substrate in various regions. These various regions are then selectively exposed to receptor solutions of differing concentrations. Indicia related to the number of receptor molecules bound to the substrate are then measured. According to preferred embodiments the indicia are obtained by measurement f fluorescent intensity of a substrate exposed to fluorescently labelled receptor.

Specifically, a first derivatized substrate, or a first of a series of duplicate arrays on a single substrate, is then exposed to a receptor of interest in a solution at a first concentration. The receptor is labelled with, for example, a fluorescein marker. The substrate is exposed to the receptor via placement of a solution or suspension of the receptor in a cavity adjacent the substrate or by contacting the entire surface of the slide in bulk. The receptor will preferentially bind to certain regions of the substrate which contain complementary sequences.

Figure 3A:
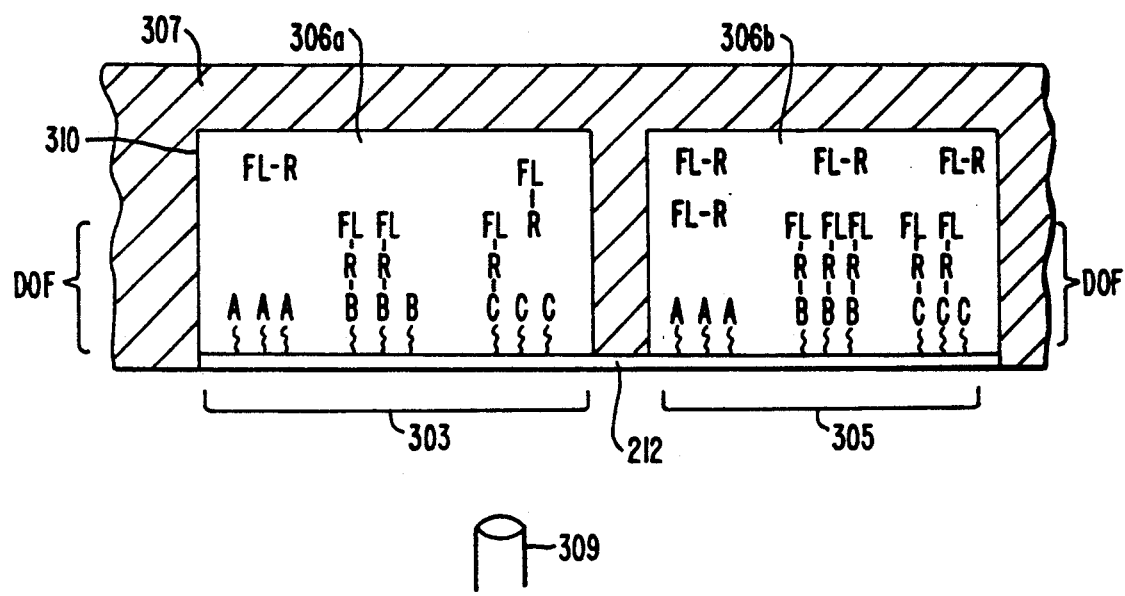

FIG. 3a schematically illustrates the process wherein duplicate arrays of polymers 303 and 305, in this case the polymers A, B, and C, have been synthesized on the substrate 212. Such polymers will, for example, be peptides having different amino acid sequences. Each of the arrays is exposed to a solution 306 containing a selected receptor R at a selected concentration in a reservoir 310. In the particular example illustrated in FIG. 3, solution 306a has a lower receptor concentration than solution 306b. The receptor is labelled with a label Fl. The various polymer arrays are exposed to different receptor concentrations through the use of channel block 307, which is mated to the substrate and has channels therein which are filled with the respective receptor solutions.

As shown in FIG. 3a, the receptor binds to polymers B and C, but not in any appreciable amount to polymer A. In the particular embodiment shown in FIG. 3a, the receptor binds to polymer B more strongly than polymer C. The higher receptor concentration of solution 306b results in more binding to both polymers than in solution 306a.

Confocal microscope 309 is used to measure the fluorescent light intensity along the surface of the substrate. Because the confocal microscope has a limited depth of field (DOF), background fluorescence from the solution receptor molecules can be limited, yet solution equilibrium or near equilibrium is ensured because the solution remains in contact with the polymer arrays. At higher concentrations of labelled receptor, interference by the solution receptor may be minimized through the use of increasing objective strength in the confocal microscope, such as an increase from 10× to 40×. Alternatively, interference may be reduced by reducing aperture size, or by labelling only a portion of the receptor.

Antibodies are typically suspended in what is commonly referred to as a "supercocktail," which may be, for example a solution of about 1% BSA (bovine serum albumin), 0.5 TWEEN TM polyoxyethylene soritan monolaurate in PBS (phosphate buffered saline) buffer. The antibodies are diluted with supercocktail buffer to a final concentration of, for example, about 0.03 to 5 $\mu$g/ml. It will be recognized that these concentrations are illustrative, and find particular application for affinities in the nano-molar range. Higher concentrations will generally be needed for lower affinity measurements.

For purposes of increasing the signal-to-noise ratio of the system, some embodiments of the invention provide for exposure of the substrate to a first labelled or unlabelled receptor followed by exposure of a labelled, second receptor (e.g., an antibody) which binds at multiple sites on the first receptor. If, for example, the first receptor is an antibody derived from a first species of an animal, the second receptor is an antibody derived from a second species directed to epitopes associated with the first species. In the case of a mouse antibody, for example, fluorescein labelled goat antibody or antiserum which is antimouse may be used to bind at multiple sites on the mouse antibody, providing several times the fluorescence compared to the attachment of a single mouse antibody at each binding site. This process may be repeated again with additional antibodies (e.g., goat-mouse-goat, etc.) for further signal amplification.

Figure 3B:
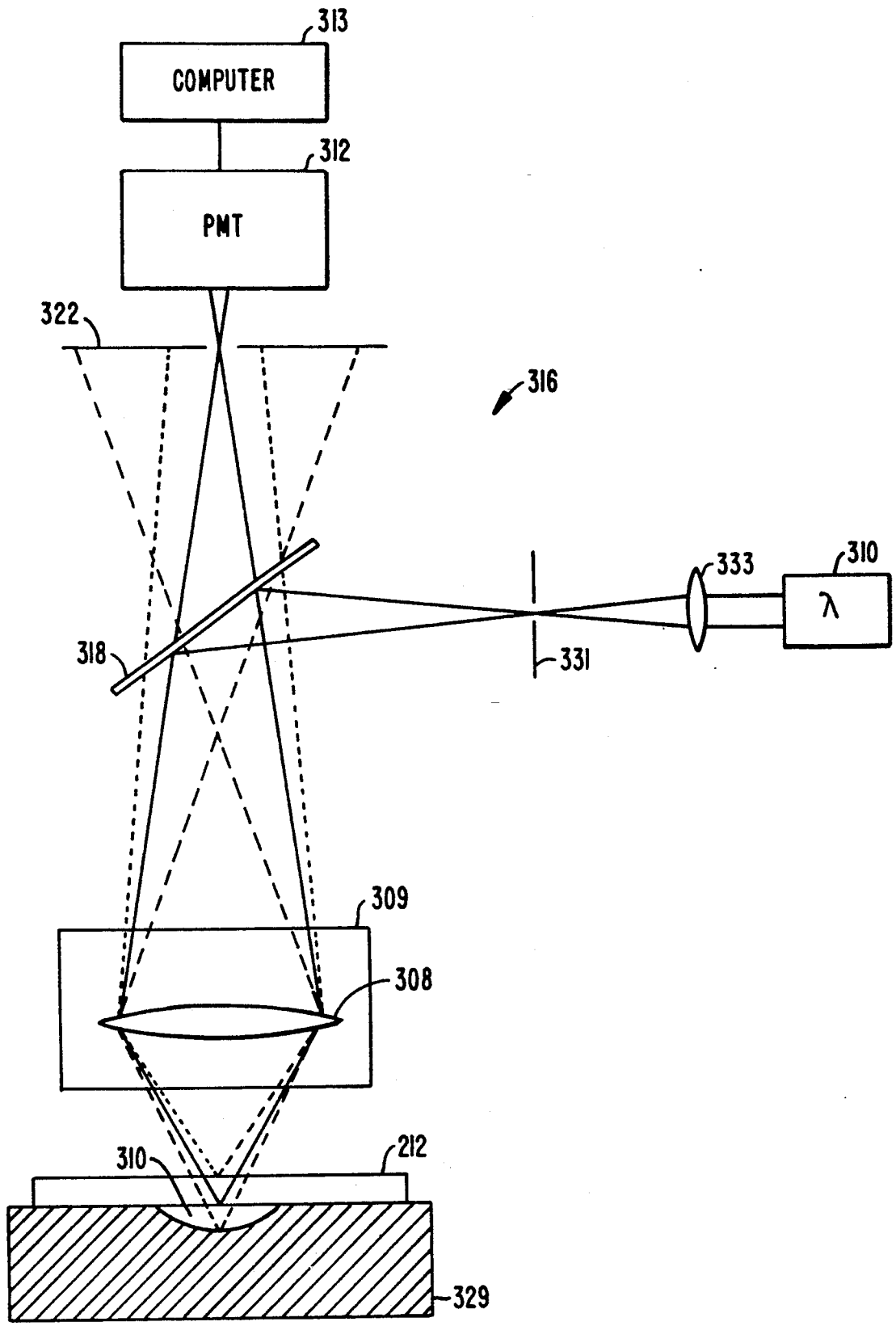

FIG. 3b illustrates a fluorescence detection device 316 for detecting fluorescein-labelled receptors on a substrate in greater detail. The substrate 212 is placed on a flow-cell 329 with one or more reservoirs 310. The reservoir(s) is filled with a receptor solution at a selected receptor concentration. In the case where multiple arrays are synthesized on a single substrate, the flow cell isolates the receptor solutions of different concentrations on the different arrays.

The substrate is placed under a microscope which includes one or more objectives 308. Light (about 488 nm) from a laser 310, which in some embodiments is a model no. 2020-05 argon ion laser manufactured by Spectraphysics, is focused on a pinhole 331 with a lens 333 and, thereafter, is directed at the substrate by a dichroic mirror 318 which passes greater than about 520 nm light but reflects 488 nm light. Dichroic mirror 318 may be, for example, a model no. FT510 manufactured by Carl Zeiss. Light reflected from the mirror then enters the microscope 309 which may be, for example, a model no. Axioscop 20 manufactured by Carl Zeiss. Fluorescein-marked materials on the substrate will fluoresce >520 nm light, and the fluoresced light will be collected by the microscope and passed through the mirror. The fluoresced light from the substrate is then directed through a wavelength filter (not shown) to reduce stray laser light and, thereafter, through an aperture plate 322. The wavelength filter may be, for example, a model no. OG530 manufactured by Melles Griot and the aperture plate may be, for example, a model no. 477352/477380 manufactured by Carl Zeiss. As shown, the system is confocal, providing a limited depth of field such that background noise is reduced or eliminated.

The fluoresced light then enters a photomultiplier tube 312 and photons are counted. The substrate is then moved to a subsequent location and the process is repeated. In preferred embodiments the data are acquired every 1 to 100 $\mu$m with a data collection diameter of about 0.8 to 10 $\mu$m preferred. In embodiments with sufficiently high fluorescence, a CCD charge coupled device detector with broadfield illumination is utilized. A computer 313 is utilized to store and process the data obtained with the system.

By counting the number of photons generated or otherwise gathering light-intensity data in a given area in response to the laser, it is possible to determine where fluorescein-marked molecules are located on the substrate while simultaneously rejecting most of the background fluorescence from the bulk solution, and determine a number of fluorescence counts for a given receptor concentration. Moreover, using the techniques disclosed herein it becomes possible to quantitatively determine the binding affinity of a receptor to a ligand, as well as specific on- and off-rates for binding.

According to one aspect of the invention, several substrates are fabricated, each having a common group of polymers synthesized thereon. Merely as a specific example, each of the substrates may have all of the pentapeptides of a given basis set of monomers. Each of the substrates is exposed to a receptor of interest, such as an antibody, but each substrate is exposed to the receptor via a solution having a different receptor concentration.

According to preferred embodiments, arrays of polymers are duplicated on a single substrate and the flow cell directs receptor solutions at different concentrations to each of the arrays simultaneously.

FIGS. 3c illustrates a preferred flow cell 329. As shown, the flow cell includes a plurality of reservoirs 310. Each reservoir is aligned with a preferably identical polymer array on the substrate which is to be evaluated for binding affinity. Around each of the reservoirs, O-rings 335 are placed and are used to seal the substrate to the flow cell. The substrate (not shown) may be secured to the upper surface of the flow cell with, for example, clamps, vacuum, or the like.

Each reservoir is connected to a flow channel 337 which is used to inject the receptor solution into the reservoir and, upon completion of the fluorescence intensity measurements, flush the receptor solution out of the reservoir. According to preferred embodiments, each flow channel is used for exposure to a receptor of a different concentration. Multiple receptor ligand analyses can be performed on a single ligand array, providing that one increases the receptor concentration each time the array is used.

Binding affinity should be determined only after the solution has reached equilibrium. Accordingly, in some embodiments the solution is left in contact with the substrate for a long period of time (e.g., about 24 hours). In some embodiments, this process is accelerated by placing the substate on a shaker table, or placing a small magnetic stirrer in a flow cell near the surface of the substrate.

Surface fluorescence intensity is recorded as photon counts for each slide while exposing the slide to the equilibrated labelled antibody or other receptor solution. Using the techniques disclosed herein and a slide which has a matrix of, for example, peptides synthesized on the surface thereof, it is possible to determine quantitatively the binding affinity of the peptides which have affinity to a fluorescently-tagged receptor using the data at different concentrations for each peptide.

Data representing a fluorescence intensity map as a function of location and receptor solution concentration are stored in the same or a different programmed digital computer for each peptide or other polymer on the substrate. Appropriate "plots" are then made indicative of a relationship between receptor concentration and fluorescence intensity. From these plots, it becomes possible to determine the relative binding affinity of each synthesized polymer to the receptor. It will be recognized by those of skill in the art that when the present disclosure refers to making a "plot" relating two variables, such plots will often never be printed, but will instead be generated in the form of relationships and data stored in a programmed digital computer from which binding affinity is determined.

A form of the Langmuir equation is utilized to determine binding affinity between a receptor and a ligand. Manipulation of the equation can produce a linear form, so either a linear or non-linear relationship can be used. Therefore, according to a preferred embodiment of the invention, a substantially linear relationship can be used between receptor solution concentration and fluorescence intensity to determine the binding affinity of the receptor/ligand pair. The non-linear model provides a more robust fit to the data.

Given a solution of receptor molecules R which adsorb to a surface of "identical and independent" unbound ligand sites S to form a bound ligand-receptor pair RS:

$$R + S \underset{k_d}{\overset{k_a}{\rightleftharpoons}} RS$$

where:
$k_a$ is the foward reaction rate of association (in molar units); and
$k_d$ is the dissociative rate.

At equilibrium:

$$K_a[R][S] = k_d[RS]$$

Therefore:

$$\frac{[S]}{[RS]} = \frac{k_d}{k_a} \cdot \frac{1}{[R]}$$

where:
[R] is the concentration of the receptor;
[S] is unbound substrate site density or number; and
[RS] is site density of receptors bound to the substrate.

Substituting for the total number of sites $[S]_o$, $[S]_o = [S] + [RS]$ and $$K_d = \frac{k_d}{k_a},$$

where $K_d$ is the dissociation constant:

$$\frac{[S]_o - [RS]}{[RS]} = \frac{K_d}{[R]}.$$

Rearranging the equation:

$$\frac{[S]_o}{[RS]} = 1 + \frac{K_d}{[R]}.$$

Defining the fractional surface coverage $$\Theta = \frac{[RS]}{[S]_o} : \Theta = \frac{1}{1 + \frac{K_d}{[R]}}.$$

The fluorescence intensity I can be scaled to $\Theta$ by a correction factor $I_{max}$, where $I_{max}$ is saturation fluorescence intensity. Rearranging to a linear form:

$$\frac{I}{[R]} = \frac{I_{max}}{K_d} - \frac{I}{K_d}$$

where $\Theta = I/I_{max}$.

Therefore, if the ratio of intensity to receptor solution concentration is plotted on a y-axis while surface fluorescence intensity is plotted on the x-axis, the data points can be best fit by a linear function. The slope of this function is $-1/K_d$, from which $K_d$ may be easily calculated, and the intercept can be solved to obtain $I_{max}$, the saturation intensity.

The above linear and non-linear method has been implemented on a digital computer using a Passage II written by Guenther and Tigges, a commercially-available program.

It will be recognized that the present invention may also be utilized to obtain the "on-rate" of the receptor (i.e., $k_a$) which, in turn, may be utilized to determine ligand site density on the substrate. Such calculations are described in, for example, Delisi, Mol. Immunol. (1981) 18:507–511, incorporated herein by reference. Such information will be obtained through continuous monitoring of fluorescense intensity over time, using best fit data. See also Goldstein et al., "Competition Between Solution and Cell Surface Receptors for Ligands," Biophysical Journal (1989) 56:955–966, and Erickson et al., Biophysical Journal (1987) 52:657–6.62, incorporated herein by reference for all purposes.

As will be readily apparent to those of skill in the art, knowledge of the binding affinity of a receptor to a ligand will have a variety of uses. Merely by way of example, knowledge of the binding affinity of a receptor to a ligand will be used to effectively determine candidate drugs, determine if a receptor binds with equal effectiveness as a native receptor; test the molecular perturbations on mutated receptor agonists and antagonists; to rank order a family of ligands to a receptor, or a family of receptors to a particular ligand; and other applications involving molecular recognition. The method also allows quick detection of high-affinity hits, without having to investigate lower-affinity targets if not desired.

III. Examples

The following examples serve to illustrate operation of the invention:

A. Example 1

Figure 4:
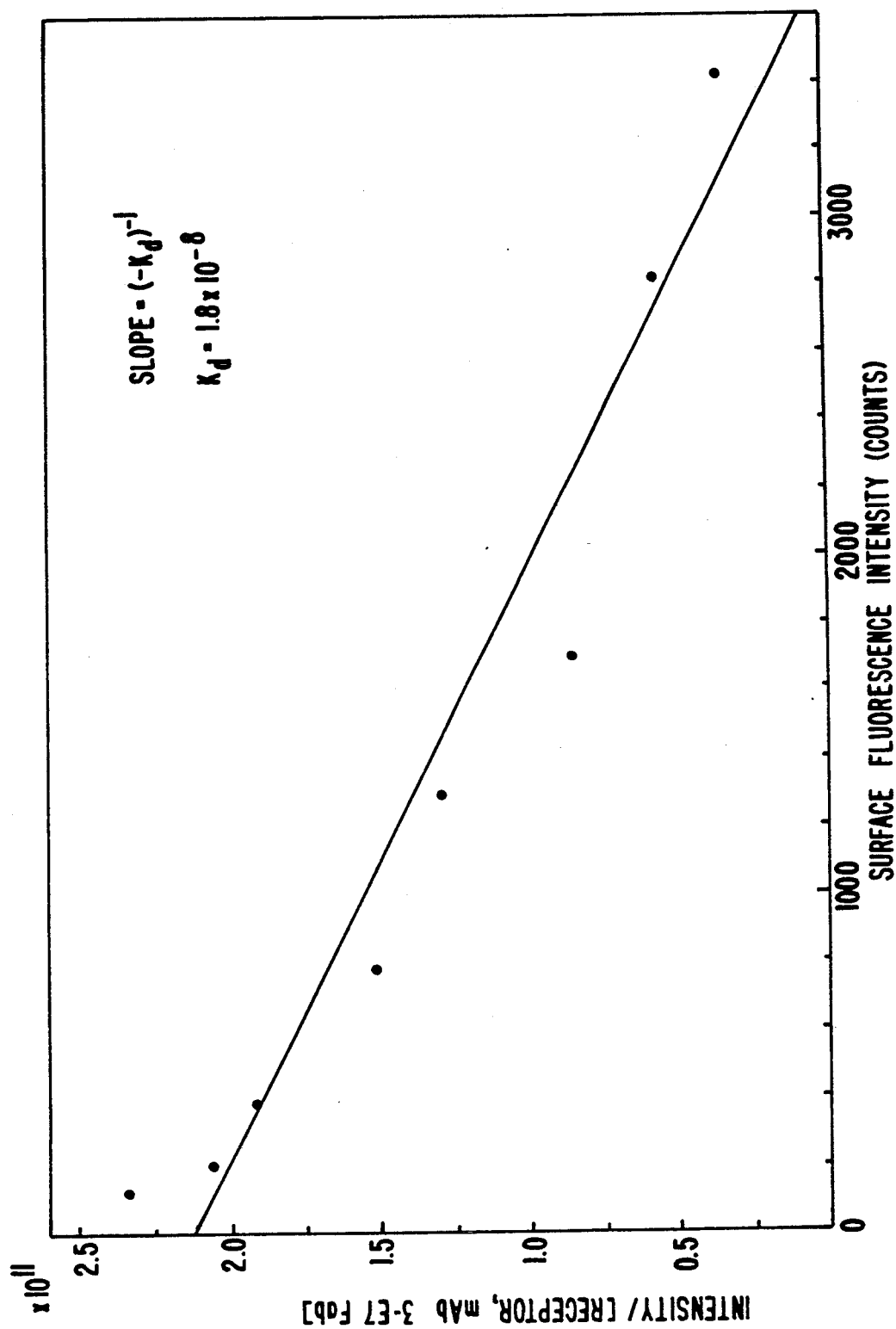
FIG. 4 illustrates an isotherm of YGGFL peptide data and, specifically, plots the ratio of fluorescence intensity to receptor concentration versus fluorescence intensity.

YGGFL (SEQ. ID NO: 1) was synthesized by the method previously described in WO 90/15070. Also, standards of immobilized pre-made YGGFL peptides were placed on a substrate. The synthesized YGGFL was exposed to the Herz antibody in varying concentrations by introducing a solution into a sealed chamber exposed to the derivatized surface of the chip and allowing the solution to reach equilibrium over about 24 hours. The solution was scanned without removing bulk solution, by using the confocal effect of focusing on the ligand surface only. FIG. 4 illustrates a plot of the ratio of fluorescence intensity to receptor concentration as a function of fluorescence intensity. Fluorescence intensity was determined as the peptide antibody fluorescence with a non-derivatized substrate background subtracted. As shown, the data fall substantially along a straight line. The slope of the best fit line through the data indicates the value of $K_d$ to be $1.8 \times 10^{-8}$ M (18 nM), which is within an acceptable range of the value of 10 nM ($1.0 \times 10^{-9}$ M) from other solution experiments.

Figure 5:
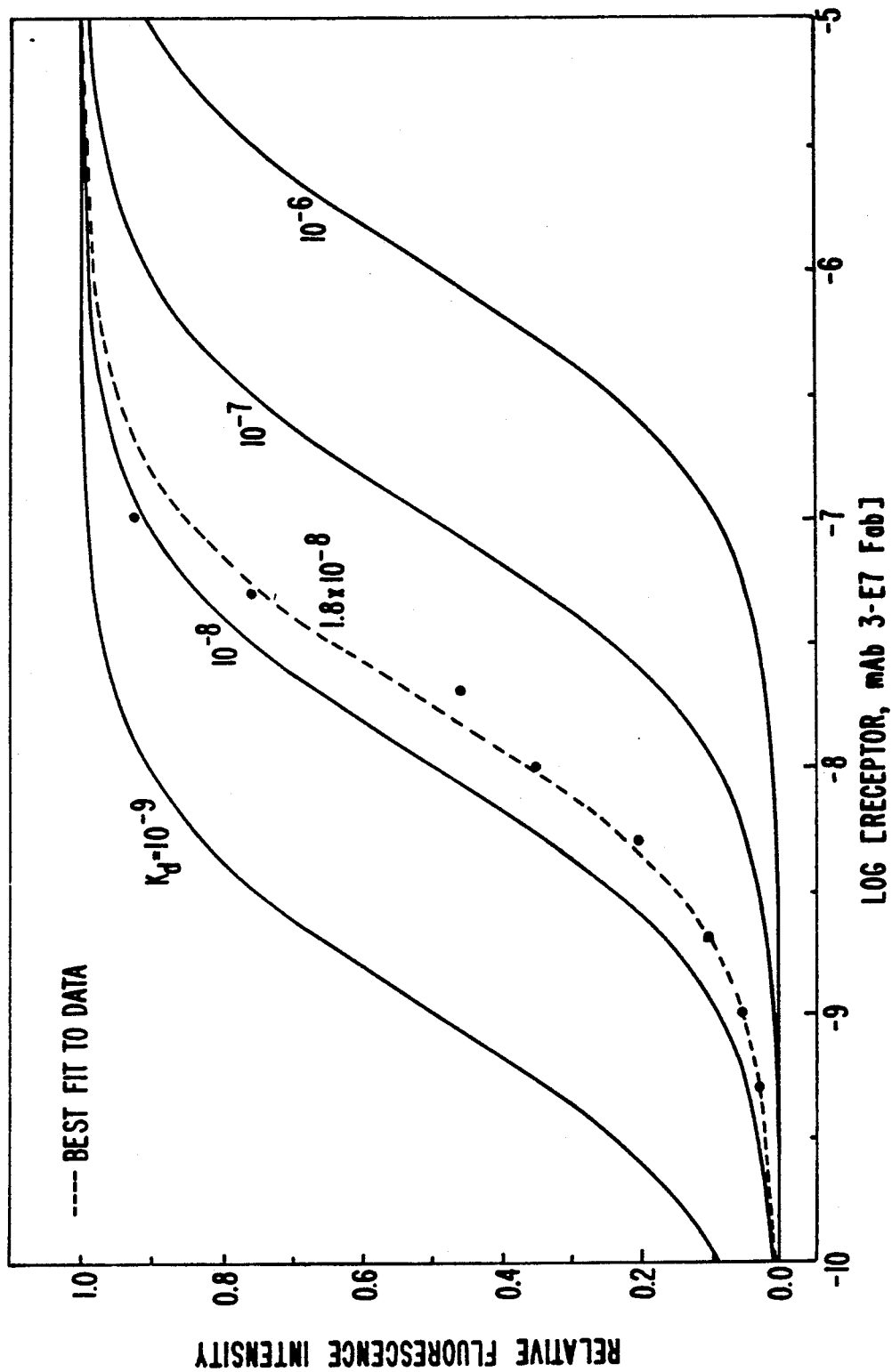
FIG. 5 illustrates an isotherm of YGGFL peptide (synthesized as a free peptide and then immobilized on a surface) information which specifically plots the normalized fluorescence intensity versus receptor concentration.

FIG. 5 illustrates a plot of relative fluorescence intensity versus the base 10 logarithm of receptor concentration, the dashed line representing a best fit of the data, which provides an alternative method of determining binding affinity. As shown, interpolating the data between the values for binding affinities of $10^{-8}$ M and $10^{-9}$ M, it is also determined that the binding affinity of YGGFL to Herz antibody is about $1.8 \times 10^{-8}$ M.

B. Example 2

Figure 6:
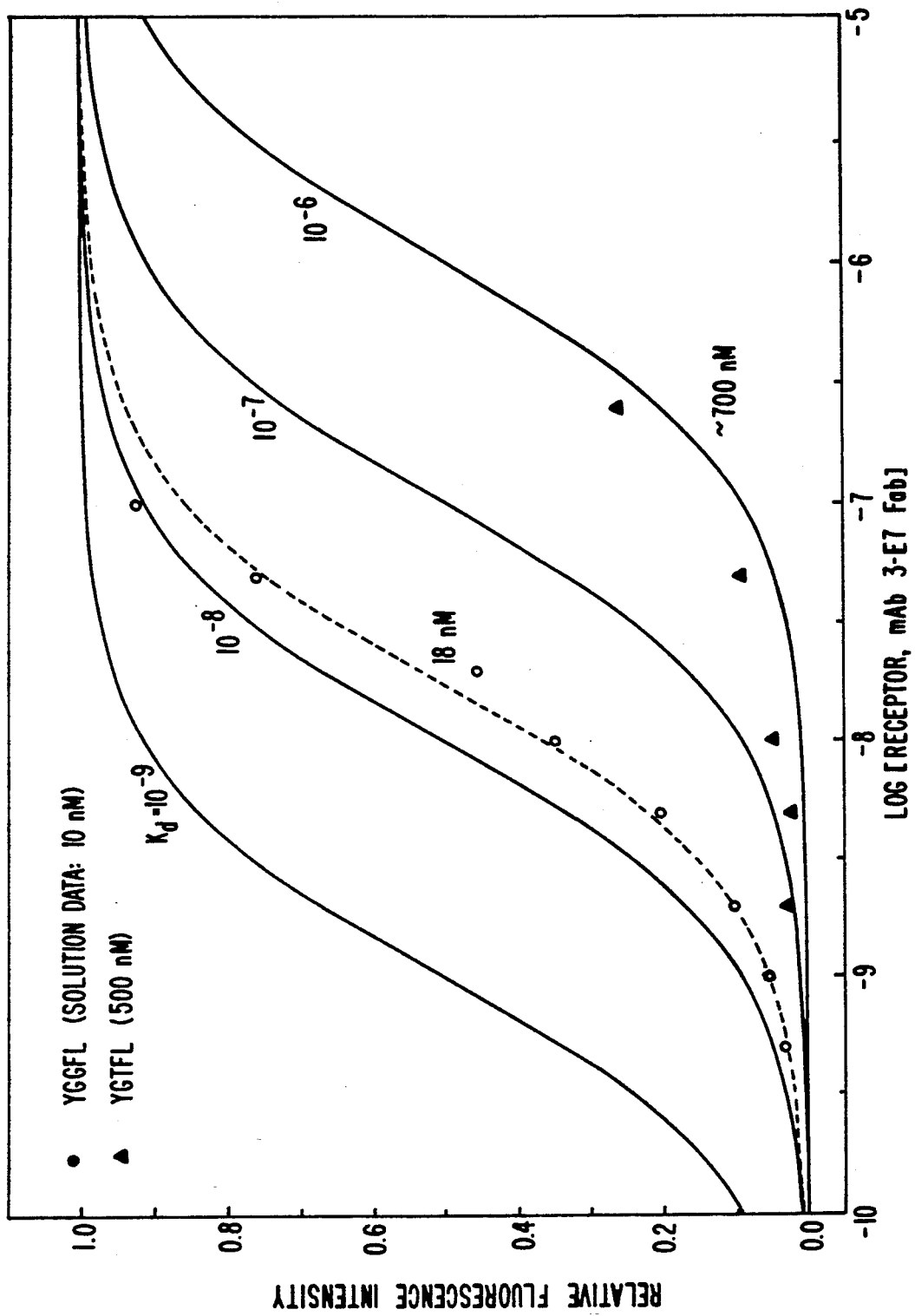
FIG. 6 illustrates YGGFL and YGTFL isotherms.

FIG. 6 illustrates data for chips having YGGFL and YGTF (SEQ. ID NO: 2) sequences synthesized on different chips using the above described methods and, thereafter, exposed to the Herz antibody. As shown, the Herz antibody was found to have a $K_d$ equal to about $1.8 \times 10^{-8}$ M to YGGFL while having a binding affinity of only about $7 \times 10^{-7}$ M to YGTFL. This is consistent with the value of $5 \times 10^{-7}$ M from other solution experiments.

Figure 7:
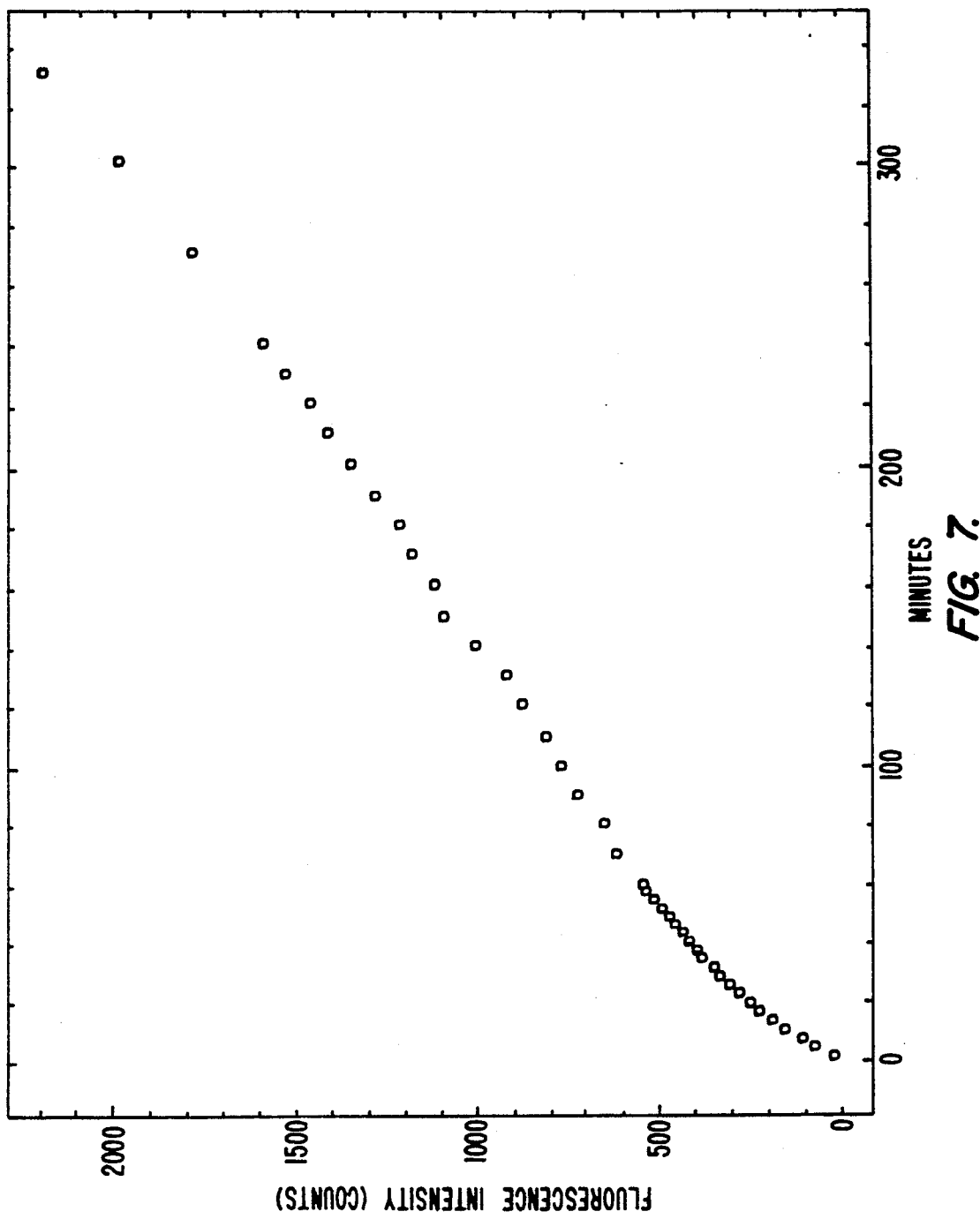
FIG. 7 illustrates kinetic antibody binding data to a YGGFL substrate.

FIG. 7 illustrates a plot from which on-rate may be determined ($k_a$). The particular plot shown therein illustrates fluorescence intensity (in counts) versus time. The data are for YGGFL binding to a fluorescein-labelled antibody, and would preferably be conducted until the graph becomes linear.

IV. Conclusion

The present invention provides a substantially novel system for directly determining the relative binding affinity of a ligand and a receptor. While specific examples have been provided, the above description is illustrative and not restrictive. Many variations of the invention will become apparent to those of skill in the art upon review of this disclosure. Merely by way of example the invention is applicable to the evaluation of a wide variety of ligand-receptor interactions. The scope of the invention should, therefore, be determined not with reference to the above description, but instead should be determined with reference to the appended claims along with their full scope of equivalents.

---

---

What is claimed is:

1. A method of determining the presence and strength of binding affinity, Kd, of a receptor, R, for a selected polymer attached at a selected region on a surface of a substrate comprising an array of polymers attached at a plurality of selected regions on the surface of the substrate, comprising the steps of:

(a) exposing the polymers to a first concentration solution of said receptor, said receptor being labeled with a fluorescent marker;

(b) irradiating the polymers with a light source;

(c) measuring fluorescence intensity of each selected region with a confocal microscope at a time sufficient for the receptor to reach specific binding equilibrium with the selected polymer;

(d) repeating steps (a)–(c) with a second concentration solution of said receptor, said receptor being labeled with the fluorescent marker, wherein the measuring step occurs while at least one of said solutions is in contact with the substrate;

(e) calculating Kd from the fluorescence intensities and the receptor concentrations for the selected polymer by solving an equation, $$\frac{I}{[R]} = \frac{I_{max}}{K_d} - \frac{I}{K_d}$$

wherein I = fluorescence intensity, [R] = receptor concentration, Imax = a saturation fluorescence intensity correction factor, to determine the presence and strength of binding of the receptor for the selected polymer.

2. The method as recited in claim 1 wherein said label is fluorescein.

3. The method as recited in claim 1 using at least two substrates, each having a common array of polymers formed thereon, said at least two substrates exposed to said receptor in different solution concentrations.

4. The method as recited in claim 1 using a substrate having duplicate arrays of polymers formed thereon, wherein each array is exposed to a different solution concentration of the receptor so that the exposing, irradiating and measuring steps at the different concentrations of the receptor occur simultaneously.

5. The method as recited in claim 1 further comprising the step of storing the fluorescence intensity for each selected polymer at each of the receptor solution concentrations in an appropriately programmed digital computer.

6. The method as recited in claim 1 wherein the calculating step further comprises plotting a linear relationship between the fluorescence intensities and the receptor concentrations.

7. The method as recited in claim 1 wherein the calculating step further comprises plotting a non-linear relationship between the fluorescence intensities and the receptor concentrations.

8. The method as recited in claim 1 wherein said second receptor concentration is higher than said first receptor concentration.

9. The method as recited in claim 1, wherein said calculating step comprises the steps of:

plotting the ratio of fluorescence intensity to receptor solution concentration on a y-axis for the selected polymer versus total surface fluorescence intensity on a x-axis in order to obtain a function curve which has a slope of $-1/Kd$;

determining the Kd of the receptor for the selected polymer from said function curve to determine the presence and strength of the binding affinity of the receptor for the selected polymer.

10. The method as recited in claim 1, wherein said receptor is indirectly labelled with the fluorescent marker by means of a second receptor labelled with the fluorescent marker, wherein the second receptor specifically binds to said receptor.

11. The method as recited in claim 1, further comprising the step of attaching said array of polymers to said plurality of selected regions on the surface of the substrate, wherein said attaching step is performed before said exposing step.

12. The method as recited in claim 11 wherein said attaching step comprises the steps of:

removing a photolytic protective group from first selected regions of said surface;

binding a first monomer comprising said photolytic protective group to said first selected regions;

removing said photolytic protective group from second selected regions of said surface, said second selected regions at least partially overlapping said first selected regions;

binding a second monomer to said second selected regions to form at least first and second polymers attached on said surface.

13. The method as recited in claim 12 further comprising the step of removing said photolytic protective group from a third selected region of said substrate and binding a fully synthesized polymer having the same monomer sequence as said first or second polymer to said third region of said substrate.

14. The method as recited in claim 11 wherein said attaching step comprises the steps of:

removing a photolytic protective group from a first selected region of said substrate;

binding a first polymer at said first selected region;

removing said photolytic protective group from a second selected region of said surface;

binding a second polymer at said second selected region.

15. The method as recited in claim 1 wherein the polymers are polypeptides.

16. The method as recited in claim 15 wherein said receptor is an antibody.

17. The method as recited in claim 15 wherein said receptor is an enzyme.

18. The method as recited in claim 1 wherein said step of measuring fluorescence intensity comprises the step of:

directing light at the polymers on said surface in a first selected region;

measuring an amount of light fluoresced from said surface at said first selected region with said confocal microscope; and repeating said steps of directing light and measuring an amount of light fluoresced for at least one selected region bearing each of the polymers.

19. The method as recited in claim 18 wherein said confocal microscope has a magnification of about 10× to 40×.

20. The method as recited in claim 18 comprising the steps of adjusting said magnification of said microscope to a higher magnification at a higher receptor concentration, and adjusting a magnification of said microscope to a lower magnification at a lower receptor concentration.

21. The method as recited in claim 1 wherein said polymers are oligonucleotides.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Tyr  Gly  Gly  Phe  Leu
1                     5

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Tyr  Gly  Thr  Phe  Leu
1                     5